United States Patent [19]
Kuwazuru et al.

[11] Patent Number: 5,531,981
[45] Date of Patent: Jul. 2, 1996

[54] METHOD FOR TREATMENT OF TERMITE

[75] Inventors: Yosei Kuwazuru, Toyonaka; Akira Igarashi, Takarazuka; Isao Minamida, Kawabe-gun, all of Japan

[73] Assignee: Takeda Chemical Industries, Ltd., Osaka, Japan

[21] Appl. No.: 322,368

[22] Filed: Oct. 13, 1994

Related U.S. Application Data

[63] Continuation of Ser. No. 190,616, Feb. 2, 1994, abandoned, which is a continuation of Ser. No. 53,361, Apr. 28, 1993, abandoned.

[30] Foreign Application Priority Data

May 1, 1992 [JP] Japan ..................... 4-155540

[51] Int. Cl.$^6$ .................. A01N 25/06; A01N 25/04; A01N 27/00
[52] U.S. Cl. ................. 424/45; 424/405; 424/408; 424/409; 424/DIG. 11; 514/365
[58] Field of Search .................. 548/204, 200; 514/305; 424/DIG. 11, 405, 408, 409, 45

[56] References Cited

U.S. PATENT DOCUMENTS

| | | | |
|---|---|---|---|
| 5,051,434 | 9/1991 | Kozo et al. | 514/357 |
| 5,166,164 | 11/1992 | Nanjo et al. | 514/565 |

FOREIGN PATENT DOCUMENTS

| | | |
|---|---|---|
| 376279 | 7/1990 | European Pat. Off. |
| 0418199 | 3/1991 | European Pat. Off. |
| 0471372 | 2/1992 | European Pat. Off. |

OTHER PUBLICATIONS

Japanese Patent Kokai (Laid-Open) No. 60-172976 (172976/85).
Japanese Patent Kokai (Laid-Open) No. 60-218386 (218386/85).
Japanese Patent Kokai (Laid-Open) No. 61-183271 (18327/86).
Japanese Patent Kokai (Laid-Open) No. 62-164605 (164605/87).
Japanese Patent Kokai (Laid-Open) No. 64-70468 (70468/89).
Japanese Patent Kokai (Laid-Open) No. 3-95104 (95104/91).
Japanese Patent Kokai (Laid-Open) No. 3-109374 (109374/91).
EPA 0418,199 Abstract.

*Primary Examiner*—Jyothsna Venkat
*Attorney, Agent, or Firm*—Foley & Lardner

[57] ABSTRACT

Safe and quite active termiticidal compositions for controlling termites comprising an effective amount of a compound of the formula:

$$\text{Cl}-\underset{S}{\overset{N}{\diagdown}}-\text{CH}_2-\underset{\underset{H}{|}}{\overset{\overset{R}{|}}{N}}\diagdown\underset{\underset{CH_3-N}{|}}{C}=N-NO_2$$

wherein R is hydrogen, a $C_{1-6}$ alkyl-carbonyl group, or $C_{1-6}$ alkoxy-carbonyl group; or a salt thereof and an an agrochemically acceptable vehicle, are provided. Methods for eradicating termites are also provided. The termiticidal composition exhibits an excellent activity in eradicating termites.

13 Claims, 1 Drawing Sheet

METHOD FOR TREATMENT OF TERMITE

This application is a continuation of U.S. application Ser. No. 08/190,616 filed Feb. 2, 1994, now abandoned which is a continuation of Ser. No. 08/053,361 filed Apr. 28, 1993 now abandoned.

FIELD OF THE INVENTION

The present invention relates to a method for controlling or eradicating termites, comprising a novel termiticidal composition more specifically the composition which contains a specific substituted guanidine derivative. The present termiticidal composition is more safe to mammals and stable against microorganisms in soil with a minimal possibility of environmental contamination than prevailing termiticides of organophosphates or pyrethroids.

BACKGROUND OF THE INVENTION

Various types of compositions for controlling termites have been used for preventing the damage to wooden buildings and constructions caused by termites. Among those types of insecticidal compositions for controlling termites, organochlorine insecticidal compositions such as dieldrin, aldrin and chlordane, had been extensively utilized worldwide and initially admired. Those compositions, however, caused environmental contamination due to an increase in the overall use of the chemicals and their indecomposable characteristics, which are prohibited in their use presently in Japan by legislation as they are classified legally as specific harmful chemical substances.

There are a number of termite control compositions for pressure process, such as CCA (mixture agent containing copper, chrome and arsenic), CFK (mixture agent containing copper, chrome and fluorine) and CFK-Z (mixture agent containing copper, chrome, zinc and fluorine). These compositions are used for the combined effects in prevention of termites and wood rot fungi, and recently their consumptions have increased. Among those compositions, particularly in the case of CCA, disposal of the waste wood became a troublesome issue as the applications increased, for which some local authorities have banned its use. Some European countries prohibited the actual applications thereof even more than ten years ago.

Of late, use has been limited to the organophosphorus compounds, carbamate compounds and pyrethroid compounds in view of relatively low toxicity and low environmental pollution potential.

Phoxim, Chlorpyrifos and Fenitrothion and the like are examples of the organophosphorus compound. Bassa and Propoxur and the like are examples of carbamate compounds. Permethrin, Tralomethrin, Bifenthrin, Cyfluthrin and Deltamethrin and the like are pyrethroid compounds in actual use.

While the outstanding problems are rather less serious in the effectiveness of organophosphorus and carbamate compounds, the problem in causing inhibition of cholinesterase activity to the workers who handle the product is still remaining unsolved because their insecticidal activities are based on the inhibition of cholinesterase.

Although it is demanded that termiticidal agents retain their preventing action on target insects for long time, it is difficult to expect that the pyrethroid compounds would have sustained insecticidal activity against termites. The lack of its sustained insecticidal activity together with its demerit in higher cost versus performance available necessitates combining use with a inexpensive synergist.

However, there are still remaining issues such as unsatisfactory properties of such agents in view of application dosage, biological activity against termites, harmlessness to human beings, etc., less potential in environmental contaminations, and limitation of applications including application frequency, as well as extensive necessitiy of not only very quick termiticidal activity but also durable actions because of use for buildings or structures such as wooden houses and cultural treasures which are partially or totally constructed with wood. Therefore, it is still desirable to solve such issues.

Practically, there is a trend that use of agents has been minimized with their minimal concentration being determined with a view toward harmlessness to human beings, etc. and less potential environmental contamination. Furthermore, since, in consideration that the prevention or eradication of termites totally depends on the effectiveness of the chemical composition and the application technology available, reduction of its absolute volume requires more accuracy in the working arrangement and it tends to make the composition more vulnerable to deterioration in the application environment. Thus, more time is needed to further reduce the effective applied volumes of such compositions.

As explained above, the prior art has never been satisfactory in view that there are various issues pertaining to compositions for controlling or eradicating termites, such as activity of the composition, safety of the operator as well as the house owner, balance between its concentration in the actual application and cost or sustained activity of the insecticidal composition, and so on.

SUMMARY OF THE INVENTION

In order to solve the said problems, the inventors have conducted extensive studies to examine various compounds for prohibitive activity against termites. As the result of such studies, the inventors have found out that the compound having the following formula (I):

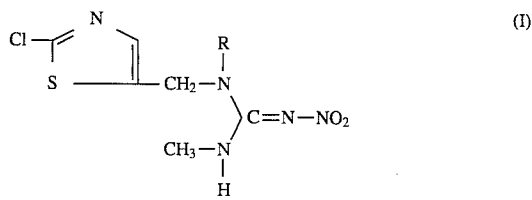

wherein R is hydrogen, a $C_{1-6}$ alkyl-carbonyl group, or a $C_{1-6}$ alkoxy-carbonyl group; or a salt thereof, exhibits a powerful effect in eradicating termites and arrived at the present invention at last after making further research works.

Thus, the present invention relates to a method for controlling termites, comprising application to termite colonies of an effective amount of a compound of the formula (I):

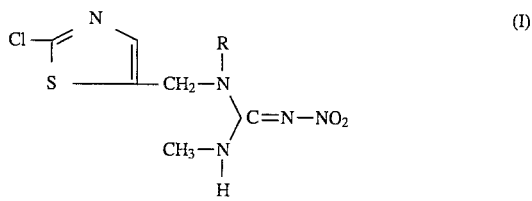

wherein R is hydrogen, a $C_{1-6}$ alkyl-carbonyl group, or a $C_{1-6}$ alkoxy-carbonyl group; or a salt thereof.

The present invention also provides a method for eradicating termites, comprising application to termite colonies of an effective amount of a compound of the formula (I) or a salt thereof. The present invention further relates to a termiticidal composition for controlling termites in their colonies, comprising an effective amount of a compound of the formula (I):

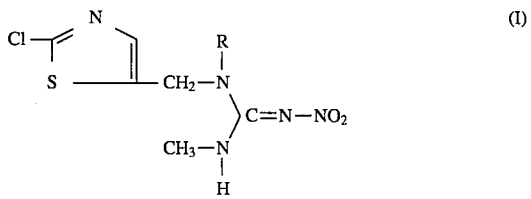
(I)

wherein R is hydrogen, a $C_{1-6}$ alkyl-carbonyl group, or a $C_{1-6}$ alkoxy-carbonyl group; or a salt thereof, and an agrochemically acceptable vehicle.

In comparison with the conventional insecticidal composition for controlling termites, the compound according to the present invention is not only superior in the characteristics required for the termiticidal composition, including soil penetration preventive capability and wood protection capability but also less toxic to all kinds of living creatures ranging from human being to animal and fish, besides it has an excellent effect in minimizing the problem concerning the environmental contamination.

The active compounds according to the present invention have unexpected advantages in that even an extremely low dose level thereof exhibits strong termiticidal activity.

The active compounds according to the present invention further have unique characteristics such as unexpected stability of its biological activity even in soil and treated wooden material, excellent durability thereof, lower potential for environmental contamination and improved safty for operators and consumers.

Also, lower levels of the effective concentration than that of conventional compositions, but which are still sufficient for the desired activity, are an advantage in addition to the point that it is free from any inhibition on cholinesterase activity.

DETAILED DESCRIPTION OF THE INVENTION

Figure 1:
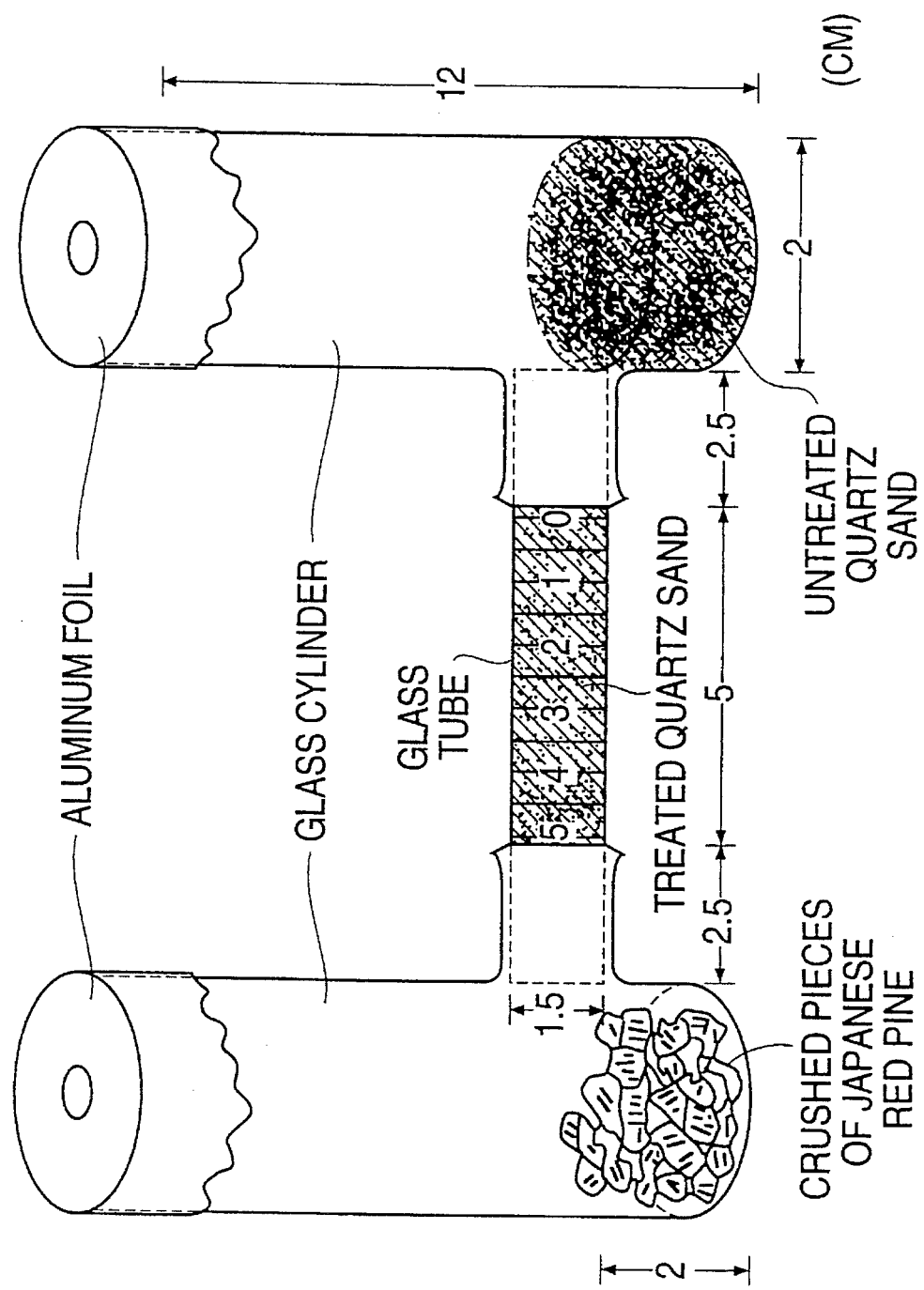
FIG. 1 illustrates an apparatus for penetration test.

The present invention relates to a method for controlling termites, comprising application to termite colonies of an effective amount of a compound of the formula (I) or a salt thereof, and particularly to a method for eradicating termites, comprising application to termite colonies of an effective amount of a compound of the formula (I) or a salt thereof.

The present invention further relates to a termiticidal composition for controlling termites in their colonies, comprising an effective amount of a compound of the formula (I) or a salt thereof, and an agrochemically acceptable vehicle.

In a preferable embodiment, the present invention relates to a method for controlling termites, comprising application to termite colonies of an effective amount of a compound of the formula (II):

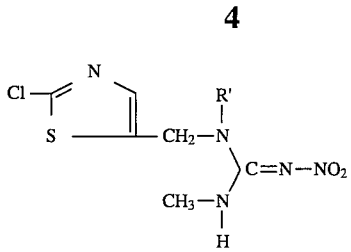
(II)

wherein R' is hydrogen, acetyl or methoxycarbonyl, or a salt thereof. The present invention further relates to a termiticidal composition for controlling termites in their colonies, comprising an effective amount of a compound of the formula (II) or a salt thereof, and an agrochemically acceptable vehicle.

In another embodiment, the present invention provides a termiticidal composition comprising an effective amount of a compound of the formula (I) or a salt thereof and an effective amount of a compound selected from the group consisting of an insecticidal organophosphorus compound, insecticidal carbamate compound and insecticidal pyrethroid compound, in admixture with a polar solvent and an agrochemically acceptable solvent with a high boiling range.

As mentioned above, the compounds according to the present invention are not only superior in the characteristics required for the termiticidal compositions, including capabilities of preventing soil penetration of termites and protecting wood material, but also are less toxic to all kinds of living creatures ranging from human being to animal and fish, and have an excellent effect in minimizing the problem concerning the environmental contamination.

The active compound according to the present invention exhibits strong sustained termiticidal activity against termites even in an extremely low dose level, unexpected stability of its biological activity even in soil and treated wooden material, and harmlessness in environment, operators and consumers. The active compound according to the present invention also exhibits excellent residual termiticidal activity even in an extremely low dose level among various applications including mixing with soil and painting on or permeating into wood.

In the formula (I), the $C_{1-6}$ alkyl-carbonyl group for R may include acetyl, ethylcarbonyl, propylcarbonyl, butylcarbonyl, pentylcarbonyl, hexylcarbonyl, etc. and most preferably acetyl. The $C_{1-6}$ alkoxy-carbonyl group for R may include methoxycarbonyl, ethoxycarbonyl, propoxycarbonyl, butoxycarbonyl, pentoxycarbonyl, hexanoxycarbonyl, etc. and most preferably methoxycarbonyl.

Among the compounds in accordance with the present invention, preferable examples thereof may include the following compounds:

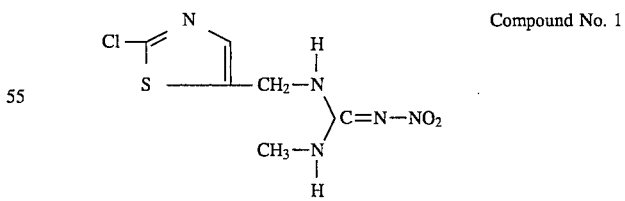

Compound No. 1

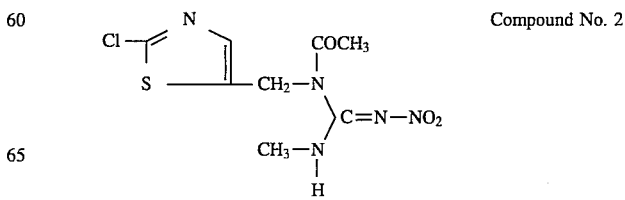

Compound No. 2

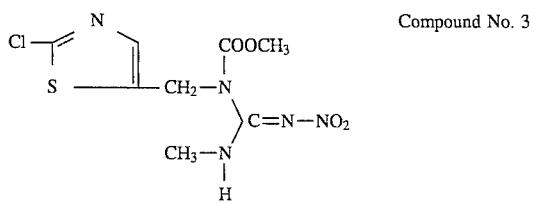

Compound No. 3

The above compound may be used in the form of a salt. As such salt, any type may be used so far as it is agrochemically acceptable or it does not badly impair the environment of the earth. The salt may be conventional. For example, it is possible to use the salt of inorganic acids such as hydrochloric acid, hydrobromic acid, hydroiodic acid, phosphoric acid, sulfuric acid and perchloric acid, or the salt of organic acids such as formic acid, acetic acid, tartaric acid, malic acid, citric acid, oxalic acid, succinic acid, benzoic acid, picric acid, methanesulfonic acid and p-toluenesulfonic acid.

The target termites of the agrochemical composition of the present invention may include various insects belonging to Isoptera and causing harm identified as the damage by the act of termite, for example, *Coptotermes formosanus, Glyptotermes satsumensis, Reticulitermes miyatakei, Reticulitermes speratus,* and *Odontotermes formosanus.*

The termiticidal composition according to the present invention may be employed in any and all forms suitable for conventional termiticidal compositions for controlling termites. In other words, suitable forms of the termiticidal composition according to the present invention include various forms such as wettable powder, emulsion, oil, paste, painting, suspension, powder, granule, high effervescent composition, non-aqueous solution, microcapsule or microsphere composition and the like.

These termiticidal compositions may be produced in accordance with well known processes in the prior art and may be prepared depending upon the purpose of respective application. Suitable compsitions or formulations are selected depending on application subjects such as timber and soil or_treatments such as painting, spraying, dipping, injection, sprinkling, admixing, and the like.

At present, the termiticidal compositions for controlling termites are roughly classified as those for soil treatment, wood treatment and coating treatment. For the soil treatment, an emulsion, powder, granule, suspension, microcapsule or microshere is preferable and for wood treatment, a non-aqueous solution is preferred and for coating treatment, a macromolecular compound mixed composition containing the effective ingredient is preferable.

In preparation of the composition for controlling termites in accordance with the present invention, an appropriate liquid diluent or a carrier may employed as the case may be. The liquid diluent or carrier may include organic solvents such as aromatic hydrocarbon (e.g. benzene, xylene, toluene, ethyl naphthalene, phenylxylylethane and the like), aliphatic hydrocarbon (e.g. paraffins, hexane, dichloromethylene, chloroethylene, chloroform and the like), alicyclic hydrocarbon (e.g. cyclohexane, cycloheptane and the like), alcohols (e.g. methanol, ethanol, propanol, butanol, cyclohexanol and the like), glycol ethers (e.g. ethylene glycol, propylene glycol and the like), ketones (e.g. acetone, methylketone, methylisobutylketone and the like), esters (e.g. ethyl acetate, di-2-ethylhexyladipate and the like), water and 2-ethylhexylphenylphosphate. These are used either solely or in a mixture combining 2 or more ingredients. Solvents having high boiling ranges are preferable from the viewpoint of advantages in environmental contamination and performance.

In preparation of the termiticidal composition according to the present invention, the active compound can be admixed with a polar solvent to produce an intermediate form suitable for formulations. Suitable polar solvents may include water, ketones such as acetone, amides such as dimethylformamide, sulfoxides such as dimethylsulfoxide, and the like.

It is preferred that, in the preparation of the termiticidal composition according to the present invention, the active compound is admixed with a strong polar solvent such as dimethylformamide or dimethylsulfoxide to produce an intermediate form suitable for formulations.

In addition to the above, the composition for controlling termites according to the present invention may be admixed or combined, as the case may be, with any kind of other agrochemically active ingredients and/or supplementary components or vehicles for agricultural chemical and horticulture such as a dispersing agent, spreader, suspending agent, fixing agent, wetting agent, thickenner, tacking agent, penetrant, mucilage, anti-blocking agent, agglomerating agent, antioxidant, demoisturizing agent and the like.

For the ordinary types of the vehicle (carrier) and extending agent, it is preferable to utilize, for example, mineral powder such as clay (e.g. pulverized clay and the like), talc (e.g. talcum powder, agalmatolite powder etc.) and silica (e.g. diatomaceous earth powder, mica powder, etc.), calcium carbonate, sulphur powder, urea powder and the like in individual form or in a mixture of 2 or more types. But the materials are not necessary limited to those mentioned above and it is possible to utilize any and all kind of the supplementary materials used for preparation of agricultural chemical and horticulture.

For the surface-active agent to be used as a dispersing agent, fixing agent, wetting agent, penetrating agent and the like, there may be used the surfactant of nonionic and anionic group such as soaps, for example, polyoxyethylenealkylarylether (e.g. Noigen ·EA-142: trademark; made by Di-ichi Kogyo Seiyaku k. k.), sodium alkylnaphthalene sulfonate (e.g. NewCalgen BX-C: trademark; made by Takemoto Yushi K. K.), the block copolymer of ethylene oxide and propylene oxide (e.g. Newpol PE-64: trademark: made by Sanyo Kasei K. K.), polycarboxylic acid type surfactant (e.g. Toxanon GR-30: trademark; made by Sanyo Kasei K. K.), dialkylsulfo-succinic acid ester sodium salt (e.g. Neocol SW-C: trademark; made by Dai-ichi Kogyo Seiyaku K. K.), polyoxyethylenedistyrenephenylether sulfate ammonium salt (e.g. Dixzol 60A: trademark; Dai-ichi Kogyo Seiyaku K. K.), sodium ligninsulfonate, potassium ligninsulfonate and the like are used as occasion demands.

For the surface-active agent to be used as a dispersing agent, fixing agent, wetting agent or penetrating agent, nonionic surfactant and anionic surfactant are utilized.

Specific examples thereof are mentioned below.

Nonionic surfactant

Polyoxyethylenealkylarylether (e.g. Noigen. EA-142; made by Dai-ichi Kogyo Seiyaku K. K.)

Block copolymer of ethylene oxide and propylene oxide (e.g. Newpol PE-64; made by Sanyo Kasei K. K.)

Anionic surfactant

Polycarboxylic acid type surfactant (e.g. Toxanon GR-30: trademark; made by Sanyou Kasei K. K.)

Dialkylsulfo succinic acid ester sodium salt (e.g. Neocol SW-C, made by Dai-ichi Kogyo Seiyaku K. K)

polyoxyethylenedistyrenephenylether sulfate ammonium salt (e.g. Dixzol 60A, Dixzol WK; made by Dai-ichi Kogyo Seiyaku K. K)

Sodium alkylnaphthalene sulfonate (e.g. New Calgen BX-C; made by Takemoto Yushi K. K)
Sodium ligninsulfonate
Potassium ligninsulfonate As an auxiliary fluidizing agent, PAP subsidiary agent (e.g. isopropyl ashed phosphate), talc and the like are utilized as the case may be.

As an anti-blocking agent, white carbon powder, diatomaceous earth, magnesium stearate and titanium dioxide are used as the case may be.

As an agglomerating agent, liquid paraffin, ethylene glycol, diethylene glycol, triethylene glycol, isobutylene polymer (e.g. IP solvent-2835: trademark; made by Idemitsu Sekiyu Kagaku K. K.) and the like are used as the case may be.

As a binding agent, carboxylmethylcellulose sodium salt, dextrin, alpha-starch, polyvinylalcohol, sodium ligninsulfonate, potassium ligninsulfonate and the like are used as the case may be.

As an antioxidant, dibutylhydroxytoluene, 4,4-thiobis-6-tert-butyl-3-methylphenol, butylated hydroxyanisole, paraoctyl phenol, mono (or tri) (a-methylbenzyl) phenol, 2, 6-di-tert-butyl-4-methylphenol, pentaerythrityl-tetrakis [3-(3, 5-di-t-butyl-4-hydroxyphenyl)] propionate and the like are used as the case may be.

As a dehydrating agent, anhydrous gypsum, silica gel powder and the like are used as the case may be.

As a ultraviolet absorbing agent, 2-(2'-hydroxy-5'-methylphenyl)benzotriazole, 2-ethoxy-2'-oxalic acid bis-anilide, dimethyl succinate-1-(2-hydroxyethyl)-4-hydroxy-2, 2, 6-tetramethylpiperidine condensation polymer and the like are used as the case may be.

As a ultraviolet diffusing agent, titanium dioxide and the like are used as the case may be.

In addition to the active component mentioned above, the composition for controlling termites according to the present invention may include one or more other agrochemically active components or compounds for agricultural and horticultural fields such as fungicides including organosulfur fungicides, organophosphorus fungicides, organoarsenic fungicides and organochlorine fungicides, insecticides including organosulfur organophosphorus insecticides, organochlorine insecticides, carbamate insecticides and pyrethroid insecticides, and various antibiotics or other active components for controlling termites.

Preferably, the composition for controlling termites according to the present invention may include one or more other agrochemically active insecticides or termiticides such as organophosphorus insecticides, carbamate insecticides and pyrethroid insecticides. Furthermore, the composition for controlling termites according to the present invention may be preferably used in admixture with one or more organophosphorus insecticides such as Phoxim and Chlorpyrifos, carbamate insecticides such as Bassa and Propoxur, and pyrethroid insecticides such as Cyfluthrin and Permethrin. Such admixed compositions for controlling termites according to the present invention may accomplish advantages in view of termiticides. For instance, such expected advantages may include excellent eradicative actions against termites together with high stability in soil, as well as significant preventive actions against termites. In view of above, the admixed compositions for controlling termites according to the present invention may accomplish advantageously quick and long lasting termiticidal actions against the target. Further, such admixed compositions for controlling termites according to the present invention may reduce application doses of agents, thereby solving the issues pertaining to environmental contaminations and human health, together with minimizing adverse effects of the agent significantly.

Such admixed compositions for controlling termites according to the present invention may also have advatageous properties in view of preparing formulations. Expected examples of such properties may include improvement on solubility or dispersibility of the active substituted guanidine derivative according to the present invention. Generally, oily solvents and media with high boiling point are preferred in the field of compositions for controlling termites in view of harmlessness to the environment and performance. When such oily solvents or media with high boiling point are employed in the composition for controlling termites according to the present invention, it is necessary to dissolve or disperse homogeneously the active substituted guanidine derivative according to the present invention in such solvents. However, it is hard to do so. Admixture of one or more organophosphorus insecticides such as Phoxim and Chlorpyrifos, carbamate insecticides such as Bassa and Propoxur, and/or pyrethroid insecticides such as Cyfluthrin and Permethrin may accomplish unexpected advantages. Such examples of the advantage may include reduction of or freedom from the polar solvent upon preparation of the composition for controlling termites according to the present invention, etc.

Preferably, the organophosphorus insecticide, carbamate insecticides and pyrethroid insecticide may be admixed respectively from 0.05 to 50:1 weight ratio per active substituted guanidine derivative according to the present invention and specifically from 0.1 to 10:1.

In an embodiment of the termiticidal composition according to the present invention, the agrochemically acceptable vehicle is a small amount of polar solvents and a larger amount of hydrocarbon solvents with high boiling range.

Examples of such polar solvents may include dimethylformamide, cyclohexanol, benzylalcohol, tetrahydrofurane and the like. Examples of such hydrocarbon solvents are solvents which have high boiling ranges. Preferable examples of such solvents are aromatic solvents such as Solvesso #100 (tradename: Exxon Chemical, boiling range 164 (initial boiling point)–176 (end boiling point) ° C.), Solvesso #150 (tradename: Exxon Chemical, boiling range 188°–209° C.), Solvesso #200 (tradename: Exxon Chemical, boiling range 231°–275° C.), Alkene 56N (tradename: Nippon Oil Chemical K. K., boiling range 267°–303° C.), Alkene 60N (tradename: Nippon Oil Chemical K. K., boiling range 270°–322° C.), or paraffinic solvents such as Exxon Naphtha No. 5 (tradename: Exxon Chemical, boiling range 154°–197° C.), Exxon Naphtha No. 7 (tradename: Exxon Chemical, boiling range 202°–265° C.), and the like.

An amount of the compound (I) of the present invention relative to the whole composition is about 0.005 to 10 parts, preferably 0.005 to 5.0 parts, more preferably 0.01 to 3.0 parts by weight per 100 parts by weight of the whole composition.

An amount of the polar solvent relative to the whole composition is about 0 to 50 parts, preferably 0 to 20 parts by weight per 100 parts by weight of the whole composition.

An amount of the hydrocarbon solvent relative to the whole composition is about 0 to 99 parts, preferably 50 to 99 parts by weight per 100 parts by weight of the whole composition.

The termiticidal composition according to the present invention can be applied to various colonies of termites in a preventive or eradicative manner. For eradication of termites, the admixed compositions of the active compound (I) with the organophosphorus insecticide, carbamate insecticides and/or pyrethroid insecticide may be preferably employed.

The colonies of termites may be in a soil or building. Representative target buildings have at least a portion composed of wood. The places to be treated with the termiticidal composition according to the present invention include areas around or underneath wooden houses or buildings. The soils or grounds on which a building is planned are preferably pretreated with the termiticidal composition according to the present invention prior to construction.

The active compound for controlling termites according to the present invention is applied as a soil treatment agent in the concentration of 0.01 to 5 weight percent, preferably in the range of 0.05 to 3 weight percent. For a wood treatment, the said compound is used with 0.01 to 5 weight percent, preferably 0.05 to 3.0 weight per cent out of 100 weight part of the product. If necessary, a popular wood preservative may additionally be included. In addition to the above, vermin repellent, synergist, antioxidant, stabilizer such as ultraviolet absorbing agent, emulsifier, coloring agent, natural or synthetic resin, thickenner, mucilage, deodorizer and aromatics may be used as the case may be.

Methods and quantities used in the case of the ordinary termiticidal component against termites may be applied to the termiticidal component for controlling termites according to the present invention, but the spreading quantity can be reduced in the latter case. For example, it is more than enough to use 1 to 50 g/m² of the active ingredient for soil treatment and 0.01 to 5 g/m² of the active ingredient for wood treatment.

The termiticidal composition for controlling termites containing the active compound (I) in accordance with the present invention may be applied to the wooden buildings safely and advantageously in consideration that it indicates an extremely stronger termiticidal effect beyond expectation and shows its activity even in much lower concentrations than the known termiticidal composition for controlling termites and causes rather limited environmental problem, and furthermore, its active effectiveness against termite is long-lasting once it is applied.

The effectiveness of the compounds No. 1, No. 2 and No. 3 are shown in examples as follows.

Example 1

Having added 1.5% Bactoagar (trade name) solution to quartz sand (which passed 60 mesh screen), the mixture was well agitated and moisture content was adjusted to be approximately 5% to prepare the treated quartz sand. The ratio of the solution to the quartz sand was 1 ml to 3 g.

The respective chemical compound dissolved in ethyl acetate was admixed with the treated quartz sand. The concentration of the respective compound was set at 10 ppm as against the total weight of quartz sand on dry basis.

Two grams each of the treated quartz sand as the control and the sample quartz sand were laid with 5 mm width space in the center of laboratory dish which had been sterilized in advance by dry heating.

Ten termite workers of *Coptotermes formosanus* SHIRAKI collected at random from their nest were thrown onto the said quartz sand.

Having put each laboratory dish in a vessel containing water in the bottom, the vessel was kept in a thermoregulated room maintained at 28°±2° C. for 14 days and the health condition and number of death of the termite workers were recorded through observation in every 2 hours, 8 hours in total, in the first day and every 24 hours in the second day onwards. This procedures were triplicated.

The time required till 100% of the sample termites were knocked down and killed was shown in the Table 1.

TABLE 1

| Test compound | Time of death | Time of knock down |
| --- | --- | --- |
| 1 | One day | Less than 2 hours |
| 2 | Two days | Less than 2 hours |
| 3 | Two days | Less than 2 hours |
| No treatment | More than 14 days | More than 14 days |

The composition according to the present invention proved to have a sufficient termiticidal effect.

EXAMPLE 2

Having dried quartz sand (which passed 20 mesh screen) at the temperature of 60°±2° C. till the weight reaches a constant level, 3 parts in weight of water was added to 12 parts in weight of the said sand to prepare the sample of untreated quartz sand.

The sample quartz sand was prepared in the following manner.

The dry quartz sand was prepared as above mentioned. Each composition was dissolved in ethyl acetate to the concentration of 0.004% and then 3 parts in weight of the solution was added to 12 parts of the dry quartz sand and after complete mixing, the mixture was left to stand for 2 weeks for vaporizing the solvent at a temperature.

Before testing, the sample sand was dampened to 25% moisture content.

The concentration of each compound was 10 ppm in proportion to the total dry weight of quartz sand.

Apparatus shown in FIG. 1 for conducting the test was prepared by connecting 2 pieces of glass cylinder having inside diameter of approximately 5 cm and height of approximately 12 cm with a glass tube (length of transparent part except joining part is 5 cm with the graduation made in every 0.5 mm) at about 2 cm above the bottom level.

Approximately 60 g of the untreated quartz sand prepared to contain moisture content of about 25% was put into one side of the glass cylinder of the testing apparatus which had been sterilized in advance and crushed pieces of Japanese red pine of approximately 3 g was put into the other side. The transparent central part of glass tube was filled with the said treated quartz sand or untreated quartz sand and, then, connected with the glass cylinder.

Two hundred termite workers and twenty termite soldiers of *Coptotermes formosanus* SHIRAKI collected from the colony were put into the glass cylinder containing the untreated quartz sand.

The testing vessel was kept in a thermoregulated room at the temperature of 28°±2° C. and at the humidity of not less than 70% for 3 weeks.

For each active compound, the test was repeated for 3 times. Three weeks later, an observation was made to determine penetration distance in the treated or the untreated layer regarding each set of test and penetration degree was determined in accordance with the following standard.
Penetration Degree 0: No penetration was observed.
Penetration Degree 1: Penetrated less than 1 cm.
Penetration Degree 2: Penetrated less than 2 cm.
Penetration Degree 3: Penetrated less than 3 cm.
Penetration Degree 4: Penetrated less less than 4 cm.
Penetration Degree 5: Penetrated more than 4 cm.

The result was shown in Table 2.

TABLE 2

| Test compound | Penetration Degree |
|---|---|
| 1 | 0, 0, 0 |
| 2 | 0, 0, 0 |
| 3 | 0, 0, 0 |
| Untreated | 5, 5, 5 |

The composition according to the present invention has sufficient preventive activity against penetration.

EXAMPLE 3

Each active compound was dissolved in acetonitrile to prepare 1,000 ppm solution. With this solution, sapwood pieces of Japanese red pine, which was 20 mm length, 10 mm width and 10 mm thickness and had been dried in a thermoregulated chamber at the temperature of 60°±2° C. for 24 hours prior to the said treatment, was treated by dipping so as to attain an pick-up of 110+10 g/m². The sample of the treated wood piece was then prepared by volatilizing the solvent completely.

The sapwood of Japanese red pine, having the 3 to 5 annual ring in each 10 mm thickness and two straight-grained surfaces, in the normal condition was adopted as the sample wood, of which each surface was finished smoothly and accurately using a plane so as to prepare a rectangular parallelepiped of 20 (L)±0.5× (R)±0.5×10 (T)±0.5 mm which had been dried in a thermoregulated chamber at the temperature of 60°±2° C. for 24 hours prior to the said treatment. Both samples of the treated wood piece and untreated wood piece were dried at the temperature of 60°±2° C. till they reached constant weight level and after leaving them in a desiccator for about 30 minutes their weights (W1) were measured to 0.01 g, to the second decimal place, which was accepted as the test sample.

As a container for the test, a cylinder made of acrylic resin with diameter of 8 cm and height of 6 cm was employed after stopping up one of its end with hardened plaster in thickness of approximately 5 mm, then the said cylinder was placed in a container with a cover (small holes were made for ventilation) in which wet cotton (adding 130 to 150 ml of water to 100 g of sanitary cotton) had been laid down in the height of approximately 2 cm.

After placing the treated test pieces or the untreated test pieces one by one keeping its edge grain surface up and down on the plaster in the container prepared as above, 150 termite workers and 15 termite soldiers of *Coptotermes formosanus* SHIRAKI were thrown into the cylinder.

Twenty one days later, the test samples were taken out of the container and substances attached to the surface of the test sample was carefully removed and then dried at the temperature of 60°±2° C. till its weight reached the constant level and kept in the desiccator for about 30 minutes, thereupon its weight (W2) was measured to 0.01 g, accurately.

Weight reduction ratio of the wood was calculated in the following formula, which was expressed by the degree of damage in accordance with the following standard.

$$\text{Weight reduction ratio of wood} = \frac{W1 - W2}{W1} \times 100$$

Damage degree 0: Reduction ratio of wood is less than 3%
Damage degree 1: Reduction ratio of wood is 3% or more and less than 10%
Damage degree 2: Reduction ratio of wood is 20% or more less than 20%
Damage degree 3: Reduction ratio of wood is 20% or more
Mortality was obtained with the following formula.

$$\text{Mortality (\%)} = \frac{\text{Number of dead termite worker}}{150} \times 100$$

Result is shown in Table 3.

TABLE 3

| Test compound | Damage degree | Mortality |
|---|---|---|
| 1 | 0 | 100 |
| 2 | 0 | 100 |
| 3 | 0 | 100 |
| Untreated | 3 | 8 |

The composition according to the present invention has sufficient capability of protection against termites.

EXAMPLE 4

Having added 1 ml of 1.5% Bactoagar (trade name) solution to 3 g of quartz sand (which passed 60 mesh screen), the mixture was well agitated to effect uniform blending and water content was adjusted to about 5%, which was adopted as the treated quartz sand. The chemical compound No. 1 dissolved in ethyl acetate was mixed with the treated quartz sand. The concentration of the compound was 1 ppm on the weight of the dry quartz sand.

2 g each of the treated quartz sand as the control and the sample quartz sand were laid with 5 mm width space between the both layers in the laboratory dish (diameter: 6 cm) which had been sterilized in advance by dry heating.

Ten termite workers (*Coptotermes formosanus* SHIRAKI) were thrown onto the quartz sand.

Having put each laboratory dish into the container containing water in the bottom, the container was kept at the temperature of 28±2° C. in a thermoregulated room for 17 days, and the health condition and number of death of the termite were observed and recorded in every 2 hours to 8 hours, on the first day and in every 24 hours on the second day onwards. These procedures were repeated 3 times.

The result of this test is shown in Table 4.

TABLE 4

|  | ppm | 2 hours | 4 hours | 6 hours | 8 hours |
|---|---|---|---|---|---|
| Compound No. 1 | 10 | 0-10-0 | 0-7-3 | 0-6-4 | 0-4-6 |
|  |  | 0-10-0 | 0-7-3 | 0-7-3 | 0-4-6 |

TABLE 4-continued

|  | ppm | | | | |
|---|---|---|---|---|---|
|  | 5 | 0-10-0 | 0-10-0 | 0-8-2 | 0-7-3 |
|  |  | 2-8-0 | 0-10-0 | 0-8-2 | 0-8-2 |
|  | 1 | 5-5-0 | 2-8-0 | 1-9-0 | 0-10-0 |
|  |  | 6-4-0 | 0-9-1 | 0-9-1 | 0-8-2 |
| Comparative | 10 | 0-10-0 | 0-10-0 | 0-10-0 | 4-6-0 |
| Compound: |  | 0-10-0 | 0-9-1 | 0-9-1 | 0-9-1 |
| Imidacloprid | 5 | 2-8-0 | 0-9-1 | 0-9-1 | 2-7-1 |
|  |  | 2-8-0 | 2-8-0 | 0-10-0 | 6-4-0 |
|  | 1 | 9-1-0 | 9-1-0 | 9-1-0 | 8-2-0 |
|  |  | 9-1-0 | 9-1-0 | 8-2-0 | 8-2-0 |

|  | ppm | 1 day | 2 days | 3 days | 4 days | 7 days |
|---|---|---|---|---|---|---|
| Compound No. 1 | 10 | 0-2-8 | 0-1-9 | 0-0-10 | 0-0-10 | 0-0-10 |
|  |  | 0-2-8 | 0-0-10 | 0-0-10 | 0-0-10 | 0-0-10 |
|  | 5 | 0-3-7 | 0-3-7 | 0-0-10 | 0-0-10 | 0-0-10 |
|  |  | 0-3-7 | 0-3-7 | 0-0-10 | 0-0-10 | 0-0-10 |
|  | 1 | 0-9-1 | 0-4-6 | 0-1-9 | 0-1-9 | 0-0-10 |
|  |  | 0-5-5 | 0-4-6 | 0-1-9 | 0-0-10 | 0-0-10 |
| Comparative | 10 | 7-3-0 | 6-4-0 | 4-3-3 | 0-5-5 | 0-0-10 |
| Compound: |  | 4-5-1 | 1-8-1 | 1-7-2 | 0-8-2 | 0-0-10 |
| Imidacloprid | 5 | 5-4-1 | 6-3-1 | 3-4-3 | 0-6-4 | 0-1-9 |
|  |  | 7-3-0 | 5-4-1 | 5-4-1 | 5-3-20 | 1-0-9 |
|  | 1 | 8-2-0 | 8-1-1 | 8-0-2 | 7-1-2 | 7-0-3 |
|  |  | 8-2-0 | 10-0-0 | 9-1-0 | 6-2-2 | 0-0-10 |

Number: (Healthy)-(Knock down)-(Death)

In the case of the compound No. 1, with its application of mere 1 ppm on the weight of quartz sand, the time required for knocking down of termites completely was extremely short as only 6 to 8 hours which is much superior to the case using the similar termiticidal composition available in the market that takes 3 to 4 days with 10 ppm.

In addition, the compound No. 1 is quite effective as no revival of termite from knock-down was observed in the test in contrast with some cases using the comparative compound.

Formulation Example 1

Five milligrams of Compound No. 1 is dissolved in 0.5 ml of acetone solution containing Tween 20 (trade name) and then diluted with a 3,000-fold aqueous solution of Dyne (trade name: Takeda Chemical Industories, inc.). The resultant mix is formulated to produce a flowable form.

The process may be repeated replacing acetone with DMSO and DMF, respectively and substituting the remaining portion with the above-mentioned hydrocarbon, alcohol, ketone and ether, respectively.

| Formulation Example 2 | |
|---|---|
| Compound No. 1 | 0.1 parts by weight |
| Phoxim[1] | 1.0 |
| dimethylformamide | 10.0 |
| Solvesso 150[2] | 88.9 |
| (Trademark: Exxon Chemical) | |
| Total | 100.0 parts by weight |

Phoxim[1]: organophosphorous insecticide, 0,0-dimethyl-0-(α-cyanobenzilideneamino)thiophospahate Solvesso 150[2]: aromatic petroleum solvent, b.p. 188°–209° C. mixed aniline point 15° C.

Compound No. 1 is admixed with dimethylformamide and the resulting mix is then admixed with Solvesso solution containing Phoxim to produce a formulation.

What is claimed is:

1. A method for controlling termites, comprising applying to a termite colony an effective amount of a composition comprising a compound selected from the group consisting of:

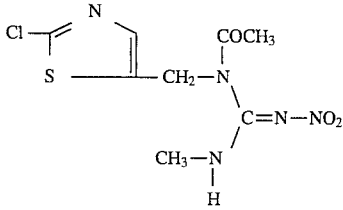

or

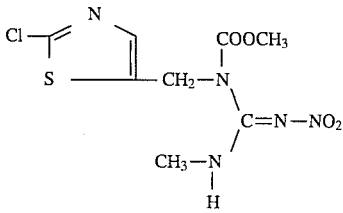

or a salt thereof and an agrochemically acceptable vehicle.

2. The method according to claim 1, in which the compound is

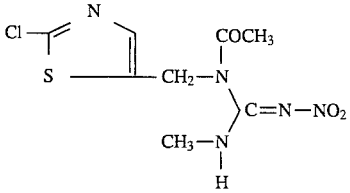

or a salt thereof.

3. The method according to claim 1, in which the compound is

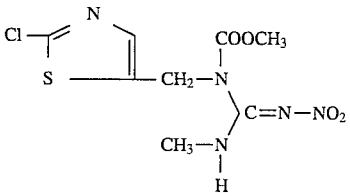

or a salt thereof.

4. The method according to claim 1, in which the termite is treated in an eradicative manner.

5. The method according to claim 1, wherein the colony is in a soil or building.

6. The method according to claim 1, in which the composition further comprises an insecticidal compound selected from the group consisting of organophosphorus insecticide, carbamate insecticide, and pyrethroid insecticide.

7. The method according to claim 6, in which the organophosphorus insecticide in Phoxim or Chlorpyrifos, the carbamate insecticide is Bassa or Propoxur, and the pyrethroid insecticide is Cyfluthrin or Permethrin.

8. The method according to claim 1, wherein agrochemically acceptable vehicle is a polar solvent or a hydrocarbon solvent.

9. The method according to claim 8, in which the amount of the polar solvent relative to the whole composition is about 0 to 50 parts by weight per 100 parts by weight of the whole composition.

10. The method according to claim 8, in which the amount of the hydrocarbon solvent relative to the whole composition is about 50 to 99 parts by weight per 100 parts by weight of the whole composition.

11. The method according to claim 1, in which the composition is selected from the group consisting of a dust, granule, wettable powder, water-dispersible granule, emulsified concentrate, oil, water soluble solid, hydrate, tablet, liquid, spray, aerosol, fumigant, painting, paste, and ointment.

12. The method according to claim 11, in which the composition is selected from the group consisting of liquid, spray, aerosol, painting, paste, and ointment.

13. The method according to claim 11, in which the dust is a DL(driftless) dust or flowable dust.

* * * * *